United States Patent

Raduechel et al.

[11] Patent Number: 5,004,752
[45] Date of Patent: Apr. 2, 1991

[54] NOVEL 9-HALOPROSTAGLANDINS, PROCESSES FOR THEIR PREPARATION, AND THEIR USE AS MEDICINAL AGENTS

[75] Inventors: Bernd Raduechel; Werner Skuballa; Helmut Vorbrueggen; Olaf Loge; Ekkehard Schilliner, all of Berlin, Fed. Rep. of Germany

[73] Assignee: Schering Aktiengesellschaft, Berlin and Bergkamen, Fed. Rep. of Germany

[21] Appl. No.: 350,951

[22] Filed: May 8, 1989

Related U.S. Application Data

[63] Continuation of Ser. No. 114,342, Oct. 30, 1987, abandoned, which is a continuation of Ser. No. 940,690, filed as PCT DE86/00122 on Mar. 19, 1986, abandoned.

[30] Foreign Application Priority Data

Mar. 22, 1985 [DE] Fed. Rep. of Germany ....... 3510978

[51] Int. Cl.$^5$ ................... C07C 177/00; A61K 31/557
[52] U.S. Cl. .................................. 514/530; 514/573; 560/118; 562/500
[58] Field of Search ......................... 560/118; 562/500; 514/530, 573

[56] References Cited

U.S. PATENT DOCUMENTS 4,444,788  4/1984  Skubulla ............................... 560/118
4,454,339  6/1984  Skubulla ............................... 560/118

Primary Examiner—Robert Gerstl
Attorney, Agent, or Firm—Millen, White & Zelano

[57] ABSTRACT

The invention relates to 9-halo-15-cycloalkyl prostaglandin derivatives of Formula I

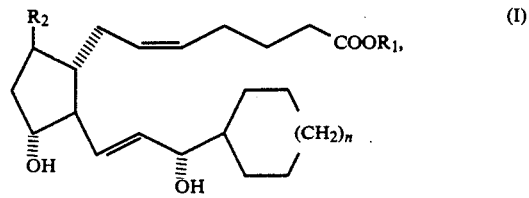

wherein
 $R_1$ is hydrogen or methyl,
 $R_2$ is fluorine or chlorine,
 n is 0 or 1, and, if $R_1$ is hydrogen, the salts thereof with physiologically compatible bases or the cyclodextrin clathrates thereof, processes for their preparation, and their pharmaceutical usage.

12 Claims, No Drawings

NOVEL 9-HALOPROSTAGLANDINS, PROCESSES FOR THEIR PREPARATION, AND THEIR USE AS MEDICINAL AGENTS

This is a continuation of application Ser. No. 07/114,342 filed Oct. 30, 1987, which is a continuation of Ser. No. 06/940,690 filed as PCT DE86/00122 on Mar. 19, 1986, both abandoned.

The present invention relates to (5Z,13E)-(9,11R, 15S)-9-halo-15-cycloalkyl-11, 15-dihydroxy-16,17,18,19,20-pentanor-5,13-prostadienoic acid derivatives, their physiologically compatible salts, and their clathrates, processes for their preparation, and pharmaceutical compositions containing same.

German Laid-Open Applications 29 50 027 and 31 26 924 claim 9-haloprostane derivatives of the following formula

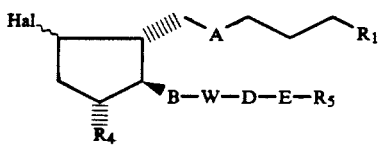

wherein
Hal is fluorine or chlorine,
$R_1$ is the residue $CH_2OH$ or

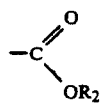

where $R_2$ means a hydrogen atom, an alkyl, cycloalkyl, aryl, or heterocyclic residue; or $R_1$ means the residue

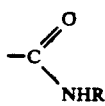

where $R_3$ means an acid residue or the residue $R_2$, and
A is a —$CH_2$—$CH_2$— or cis—CH=CH—group,
B is a —$CH_2$—$CH_2$— or trans—CH=CH— or —C≡C—group,
W is a free or functionally modified hydroxy-methylene group wherein the OH-group can be in the α- or β-position,
D and E jointly mean a direct bond or
D is a straight- or branched-chain alkylene group of 1-10 carbon atoms which can optionally be substituted by fluorine atoms,
E is an oxygen or sulfur atom, a direct bond, a —C≡C—bond, or a —$CR_6$=$CR_7$—group wherein $R_6$ and $R_7$ differ from each other and mean a hydrogen atom, a chlorine atom or an alkyl group,
$R_4$ is a free or functionally modified hydroxy group,
$R_5$ is a hydrogen atom, an alkyl, a halosubstituted alkyl, a cycloalkyl, an optionally substituted aryl or heterocyclic group and, if $R_2$ means a hydrogen atom, the salts thereof with physiologically compatible bases.

The prostaglandin derivatives from DOS's 29 50 027 and 31 26 924 are suitable, after a one-time enteral or parenteral administration, for inducing menstruation or interrupting pregnancy. They are suited for synchronizing the sexual cycle in female mammals, such as rabbits, cattle, horses, or pigs, as well as for cervix dilation as a preparation for diagnostic or therapeutic interventions.

They inhibit gastric acid secretion, exhibit cytoprotective and ulcer-healing effects, and thus counteract the undesirable consequences of non-steroidal anti-inflammatory agents (prostaglandin synthesis inhibitors).

Several ones of these compounds also have blood-pressure-lowering activity, have a regulating effect in cardiac arrhythmias, and inhibit platelet aggregation.

The 9-halo-15-cycloalkyl prostaglandin derivatives have not been mentioned by name either in DOS 29 50 027 or DOS 31 26 924 and exhibit a pharmacological characteristic deviating from that of the compounds of the cited laid-open applications, as will be discussed in detail below.

Accordingly, the invention relates to 9-halo-15-cycloalkyl prostaglandin derivatives of Formula I

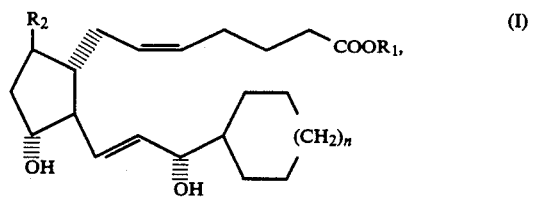

wherein
$R_1$ is hydrogen or methyl,
$R_2$ is fluorine or chlorine
n is 0 or 1, and, if $R_1$ is hydrogen, the salts thereof with physiologically compatible bases or the cyclodextrin clathrates thereof.

Suitable alkyl groups $R_3$ are straight- and branched-chain alkyl residues of 1-6 carbon atoms, such as, for example, methyl, ethyl, propyl, butyl, isopropyl, isobutyl, pentyl, isopentyl, hexyl. Preferred residues are methyl, ethyl, propyl and isopropyl.

Suitable for salt formation are inorganic and organic bases as they are known to a person skilled in the art for the formation of physiologically compatible salts. Examples that can be cited are alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)-methylamine, etc.

The invention furthermore relates to a process for the preparation of the 9-halo-15-cycloalkyl prostaglandin derivatives of Formula I, characterized by reacting a compound of Formula II

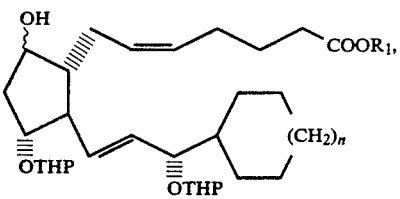# (II)

wherein the OH-group can be in the α- or β-position, $R_1$ means methyl, n has the above-indicated meanings, and THP is tetrahydropyranyl, by way of an intermediate 9-sulfonic acid ester, with a halogenide of Formula III $R_3Hal$ wherein $R_3$ is lithium, sodium or potassium if Hal is chlorine, and $R_3$ is tetra($C_1$-$C_6$-alkyl)ammonium if Hal is fluorine; and optionally subsequently, in the thus-obtained reaction products, in any desired sequence, liberating blocked hydroxy groups, saponifying the esterified carboxy group ($R_1 = CH_3$) and/or converting the free carboxy group ($R_1 = H$) into a salt or clathrate.

The reaction of the compounds of general Formula II to a 9-sulfonic acid ester takes place conventionally with an alkyl sulfonyl chloride or aryl sulfonyl chloride in the presence of an amine, such as, for example, pyridine or triethylamine, at temperatures of between $-60°$ C. and $+100°$ C., preferably $-20°$ C. to $+50°$ C. The nucleophilic substitution of the 9-sulfonate by a chlorine atom takes place with an alkali chloride, preferably lithium chloride, and by a fluorine atom with tetra($C_1$-$C_6$-alkyl)ammonium fluoride, preferably tetrabutylammonium fluoride, in an inert solvent, such as, for example, dimethylformamide, dimethylacetamide, dimethyl sulfoxide, dimethoxyethane, tetrahydrofuran, etc., at temperatures of between $0°$ C. and $100°$ C., preferably $20°$ C. to $80°$ C.

The step of splitting off the tetrahydropyranyl residue is conducted in an aqueous solution of an organic acid, such as, for example, oxalic acid, acetic acid, propionic acid, and others, or in an aqueous solution of an inorganic acid, such as, for example, hydrochloric acid. To improve solubility, a water-miscible, inert organic solvent is suitably added. Suitable organic solvents are, for example, alcohols, such as methanol and ethanol, and ethers, such as dimethoxyethane, dioxane and tetrahydrofuran. Tetrahydrofuran is preferably utilized. The splitting-off step is preferably performed at temperatures of between $20°$ C. and $80°$ C.

The prostaglandin derivatives of Formula I wherein $R_1$ means a hydrogen atom can be converted into a salt with suitable amounts of the corresponding inorganic bases with neutralization. For example, the solid inorganic salt is obtained when dissolving the corresponding PG acids in water containing the stoichiometric amount of the base, and thereafter removing the water by evaporation or adding a water-miscible solvent, e.g. alcohol or acetone.

For the production of an amine salt, which takes place as usual, the PG acid is dissolved, for example, in a suitable solvent, e.g. ethanol, acetone, diethyl ether, acetonitrile or benzene, and at least the stoichiometric amount of the amine is added to this solution. During this step, the salt is ordinarily obtained in the solid form or is isolated in the usual way after evaporation of the solvent.

For producing the clathrates, the compounds of Formula I are dissolved in a pharmacologically acceptable alcohol, preferably ethanol, and added to aqueous solutions of α-, β- or γ-cyclodextrin, preferably β-cyclodextrin, at $60°$ C. After cooling, the corresponding clathrates are crystallized and can be isolated by suctioning off and drying as solid, freely flowing crystals.

The starting compounds of Formula II are disclosed in German Laid-Open Application DOS 25 15 770.

The 15-cycloalkyl prostaglandins of Formula I are distinguished by properties typical for $PGD_2$, i.e. they show good binding action to the $PGD_2$ receptor, but poor binding to the $PGE_2$ and $PGI_2$ receptor. Studies on the bovine coronary artery and the rabbit pulmonary artery likewise point to a $PGD_2$ activity profile of the compounds of Formula I.

The compounds exhibit a blood-pressure-lowering activity upon i.v. infusion in rats.

The active compounds of this invention inhibit gastric acid secretion, exhibit a cytoprotective and ulcer-healing activity, and thus counteract the undesirable consequences of nonsteroidal anti-inflammatory agents (prostaglandin synthesis inhibitors). The exert a regulatory effect in cardiac arrhythmias and inhibit platelet aggregation.

For medical usage, the active compounds can be converted into a form suitable for inhalation, for oral and parenteral administration or local application (e.g. vaginally).

Aerosol solutions are suitably prepared for inhalation.

Tablets, dragees or capsules, for example, are suited for oral administration.

Sterile, injectable, aqueous or oily solutions are utilized for parenteral administration.

For vaginal application, suppositories, for example, are suitable and customary.

The invention thus also concerns medicinal agents based on the compounds of general Formula I and the conventional auxiliary agents and excipients.

The active agents of this invention are to serve, in conjunction with the auxiliary agents known and customary in galenic pharmacy, for example for the production of pharmaceutical preparations. The preparations can contain 0.01-50 mg of active compound.

The examples set forth below are to describe the invention in greater detail without being limiting.

EXAMPLE 1

(5Z,13E)-(9R,11R,15S)-9-Chloro-15-cyclohexyl-11,15-dihydroxy-16,17,18,19, 20-pentanor-5,13-prostadienoic Acid Methyl Ester At $0°$ C., 191 mg of p-toluenesulfonyl chloride is added to a solution of 1.098 g of (5Z,13E)-(9S,11R,15S)-15-cyclohexyl-9-hydroxy-11, 15-bis(tetra-hydropyran-2-yloxy)-16,17,18,19,20-pentanor-5,13prostadienoic acid methyl ester in 10 ml of pyridine and, after 24 hours, another 191 mg is added. The mixture is allowed to stand at $0°$ C. for a total of 48 hours, then combined with 0.1 ml of water, agitated for 2 hours, diluted with 200 ml of ether, and washed in succession with dilute sulfuric acid, water, and brine, dried over magnesium sulfate, evaporated, and the product is 1.20 g of the 9α-tosylate as a colorless oil.

IR ($CHCl_3$) 2945, 2872, 1735, 1366, 1240,

978/cm

A solution of 1.05 g of the 9α-tosylate in 45 ml of dimethylformamide is stirred with 600 mg of lithium chloride for 4 hours at 65° C. The mixture is diluted with brine, extracted with ether/hexane (1:1), the extract washed with water and brine, dried over magnesium sulfate, and evaporated under vacuum. The residue is purified by chromatography on silica gel with toluene:ethyl acetate (95:5 to 80:20), thus obtaining 520 mg of the 9β-chloro compound which is stirred for 18 hours at 32° C. with 20 ml of a mixture of acetic acid-water-tetrahydrofuran (65/35/10) to split off the tetrahydropyranyl ether blocking groups. After evaporation of the solution under vacuum, the residue is chromatographed on silica gel. With dichloromethane-acetone (9:1) as eluent, 285 mg of the title compound is obtained as a colorless oil.

IR (CHCl$_3$): 3600, 3410, 3000, 2932, 2859, 1732, 972/cm

EXAMPLE 2

(5Z,13E)-(9R,11R,15S)-9-Chloro-15-cyclohexyl-11,15-dihydroxy-16,17,18,19, 20-pentanor-5,13-prostadienoic Acid At 20° C., 220 mg of the methyl ester obtained according to Example 1 is stirred for 5 hours with a solution of 100 mg of potassium hydroxide, 0.5 ml of water, and 5 ml of ethanol. The mixture is concentrated under vacuum, diluted with 20 ml of water, adjusted to pH 4 with citric acid, and extracted with dichloromethane. The extracts are washed with water, dried over magnesium sulfate, and evaporated under vacuum. The residue is purified by chromatography on silica gel, eluting with dichloromethane/methanol (95:5), thus producing 192 mg of the title compound as a colorless oil.

IR (CHCl$_3$): 3600, 3450, 2955, 2859, 1710, 974/cm

EXAMPLE 3

(5Z,13E)-(9R,11R,15S)-9-Chloro-15-cyclopentyl-11,15-dihydroxy-16,17,18,19, 20-pentanor-5,13-prostadienoic Acid Methyl Ester Using 1.05 g of (5Z,13E)-(9S,11R,15S)-15-cyclopentyl-9-hydroxy-11, 15-bis(tetrahydropyran-2-yloxy)-16,17,18,19,20-pentanor-5,13-prostadienoic acid methyl ester as the starting material, the process is carried out as described in Example 1, thus obtaining 242 mg of the title compound as a colorless oil.

IR (CHCl$_3$): 3600, 3405, 2998, 2935, 2858, 1735, 978/cm

EXAMPLE 4

(5Z,13E)-(9R,11R,15S)-9-Chloro-15-cyclopentyl-11,15-dihydroxy-16,17,18,19, 20-pentanor-5,13-prostadienoic Acid 180 mg of the methyl ester obtained according to Example 3 is saponified by means of the method indicated in Example 2, yielding 135 mg of the title compound as an oil.

IR (CHCl$_3$) 3600, 3450, 2927, 2860, 1709, 976/cm

EXAMPLE 5

(5Z,13E)-(9R,11R,15S)-15-Cyclohexyl-11,15-dihydroxy-9-fluoro-16,17,18,19, 20-pentanor-5,13-prostadienoic Acid Methyl Ester A solution of 4.2 g of (5Z,13E)-(9S,11R,15S)15-cyclohexyl-9-tosyloxy-11, 15-bis(tetrahydropyran-2-yloxy)-16,17,18,19,20-pentanor-5,13-prostadienoic acid methyl ester (prepared according to Example 1) in 70 ml of dimethyl sulfoxide is combined with 12 mg of tetrabutylammonium fluoride (dried by repeatedly distilling off toluene under vacuum at 50° C.), and the mixture is agitated for 2 hours at 22° C. under argon. Subsequently the mixture is diluted with 400 ml of water, extracted three times with respectively 150 ml of ether/hexane (2:1), the extracts are washed with brine, dried over magnesium sulfate, and evaporated under vacuum. The residue is purified on silica gel and eluted with hexane-ethyl acetate (10:1) yielding 1.03 g of the 9β-fluoro compound which, for splitting off the blocking groups, is agitated for 18 hours at 22° C. with 25 ml of a mixture of acetic acid-water-tetrahydrofuran (65/35/10). After evaporation of the solution and purification by chromatography on silica gel with dichloromethane-acetone (10:1), 830 mg of the title compound is obtained as a colorless oil.

IR (CHCl$_3$) 3600, 3410, 2998, 2932, 2865, 1729, 976/cm

EXAMPLE 6

(5Z,13E)-(9R,11R,15S)-15-Cyclohexyl-11,15-dihydroxy-9-fluoro-16,17,18,19, 20-pentanor-5,13-prostadienoic Acid The procedure of Example 2 is followed, thus obtaining, from 500 mg of the methyl ester produced as described in Example 5, 425 mg of the title compound as a colorless oil.

IR (CHCl$_3$) 3600, 3405, 2930, 2858, 1710, 976/cm

EXAMPLE 7

(5Z,13E)-(9R,11R,15S)-15-Cyclopentyl-11,15-dihydroxy-9-fluoro-16,17,18,19, 20-pentanor-5,13-prostadienoic Acid Methyl Ester At 0° C., 191 mg of p-toluenesulfonyl chloride is added to a solution of 1.07 g of (5Z,13E)-(9S,11R,15S)-15-cyclopentyl-9-hydroxy-11,15-bis-(tetrahydropyran-2-yloxy)-16,17,18,19,20-pentanor-5,13-prostadienoic acid methyl ester in 10 ml of pyridine; the mixture is stirred further at 0° C. and, after 24 hours, combined with another 191 mg of acid chloride. After 48 hours, 0.1 ml of water is added, the mixture is stirred for 2 hours, diluted with ether, and washed in succession with dilute sulfuric acid, water, and brine, dried over magnesium sulfate, evaporated, and the thus-obtained product is 1.12 g of the 9α-tosylate as a colorless oil.

IR (CHCl$_3$): 2952, 2878, 1733, 1359, 1241, 976/cm

A solution of 1 g of the 9α-tosylate in 20 ml of dimethyl sulfoxide is combined with 3 g of tetrabutylammonium fluoride; the mixture is stirred for 2 hours at room temperature, then diluted with water, and then extracted repeatedly with ether/hexane (2:1). The combined extracts are washed with brine, dried over magnesium sulfate, and evaporated under vacuum. The residue is purified on silica gel and with hexane-ethyl acetate (85:15) 205 mg of the 9β-fluoro compound is eluted which, for splitting off the blocking groups, is stirred for 18 hours at room temperature with 5 ml of a mixture of acetic acid-water-tetrahydrofuran (65/35/10). After evaporation of the solution and purification by chromatography on silica gel with dichloromethane-acetone (85:15), 110 mg of the title compound is obtained as a colorless oil.

IR (CHCl₃) 3600, 3408, 2998, 2929, 2854, 1733, 976/cm

EXAMPLE 8

(5Z,13E)-(9R,11R,15S)-15-Cyclopentyl-11,15-dihydroxy-9-fluoro-16,17,18,19, 20-pentanor-5,13-prostadienoic Acid A solution of 85 mg of the methyl ester prepared according to Example 7 in 5 ml of ethanol is combined with 50 mg of potassium hydroxide, dissolved in 0.5 ml of water, and the mixture is stirred for 5 hours at 20° C. After concentration under vacuum, the mixture is combined with 10 ml of water, acidified with citric acid to pH 3, and repeatedly extracted with dichloromethane, dried over magnesium sulfate, and evaporated under vacuum, yielding 72 mg of the title compound as a colorless oil.

IR (CHCl₃): 3600, 3430, 2931, 2859, 1710, 974/cm

EXAMPLE 9

Tris(hydroxymethyl)aminomethane Salt of (5Z,13E)-(9R,11R,15S)-9-Chloro-15-cyclohexyl-11, 15-dihydroxy-16,17,18,19,20-pentanor-5,13-prostadienoic Acid At 65° C., a solution of 75 mg of tris(hydroxymethyl)aminomethane in 0.25 ml of water is added to a solution of 250 mg of (5Z,13E)-(9R,11R,15S)-9-chloro-15-cyclohexyl-11,15-dihydroxy-16, 17,18,19,20-pentanor-5,13-prostadienoic acid in 40 ml of acetonitrile. The mixture is allowed to cool down to 20° C. under agitation, and the solvent is suctioned off, thus obtaining 205 mg of the crystalline title compound, mp 118–120° C.

IR (KBr): 2965, 1655, 1420, 976/cm

We claim:

1. A 9-Halo-15-cycloalkyl prostaglandin derivative of Formula I

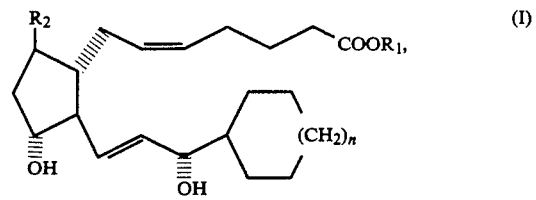

wherein
$R_1$ is hydrogen or methyl,
$R_2$ is chlorine,
n is 0 or 1, or when $R_1$ is hydrogen, a salt thereof with a physiologically compatible base or a cyclodextrin clathrate thereof.

2. (5Z,13E)-(9R,11R,15S)-9-Chloro-15-cyclohexyl-11,15-dihydroxy-16,17,18,19, 20-pentanor-5,13-prostadienoic acid.

3. (5Z,13E)-(9R,11R,15S)-9-Chloro-15-cyclopentyl-11,15-dihydroxy-16,17,18,19, 20-pentanor-5,13-prostadienoic acid.

4. Tris(hydroxymethyl)aminomethane salt of (5Z,13E)-(9R,11R,15S)-9-chloro-15-cyclohexyl-11,15-dihydroxy-16,17,18,19, 20-pentanor-5,13-prostadienoic acid.

5. A compound of claim 1, wherein n is 0.
6. A compound of claim 1, wherein n is 1.
7. A compound of claim 1, wherein $R_1$ is H.
8. A compound of claim 1, wherein $R_1$ CH₃.
9. A method of lowering blood pressure in a patient in need of such treatment comprising administering to said patient an effective amount of a compound of claim 1.
10. A method of inhibiting gastric acid secretion, or achieving a cytoprotective or ulcer healing effect in a patient in need of such treatment comprising administering to said patient an effective amount of a compound of claim 1.
11. A pharmaceutical composition comprising an amount of a compound of claim 1 effective pharmacologically and a pharmaceutically acceptable carrier.
12. A method of inhibiting platelet aggregation in a patient in need of such treatment comprising administering to said patient an effective amount of a compound of claim 1.

* * * * *